US006072088A

United States Patent [19]

Van Der Puy

[11] Patent Number: 6,072,088

[45] Date of Patent: Jun. 6, 2000

[54] CHEMICAL COMPOUNDS HAVING TWO TRIFLUOROMETHYL GROUPS

[75] Inventor: Michael Van Der Puy, Amherst, N.Y.

[73] Assignee: Alliedsignal Inc., Morristown, N.J.

[21] Appl. No.: 09/371,217

[22] Filed: Aug. 10, 1999

Related U.S. Application Data

[63] Continuation of application No. 08/864,522, May 28, 1997, abandoned.

[51] Int. Cl.[7] .................... C07C 41/00

[52] U.S. Cl. .................... 568/685; 568/677; 568/684; 568/683; 568/844; 570/134; 570/135; 570/136

[58] Field of Search .................... 568/677, 684, 568/685, 683, 844; 570/134, 135, 136

[56] References Cited

U.S. PATENT DOCUMENTS

| | | | |
|---|---|---|---|
| 2,407,246 | 9/1946 | Benning | 260/653 |
| 3,502,721 | 3/1970 | Krespan | 260/566 |
| 3,696,154 | 10/1972 | Anderson | 260/609 |
| 3,705,917 | 12/1972 | Woolf | 260/453 |
| 5,545,769 | 8/1996 | Baker | 570/134 |

FOREIGN PATENT DOCUMENTS

| | | |
|---|---|---|
| 64-61706 | 3/1989 | Japan . |
| 95/05353 | 2/1995 | WIPO . |

OTHER PUBLICATIONS

Lovelace, "Aliphatic Fluorine Compounds," pp. 55, 96, 99, 180–200, 211 217, 241 &255, 1958.

*Primary Examiner*—Michael L. Shippen

*Attorney, Agent, or Firm*—Colleen D. Szuch; Marie L. Collazo

[57] ABSTRACT

A compound having the formula:

$$CF_3CH_{2-w}(H_{1-x}CH_{2-y}R_mR'_nCH_{1-z})_pH_{2-q}CF_3$$

wherein w=0, 1 or 2; x=0 or 1; y=0, 1 or 2; m=0, 1 or 2; n=0 or 1; z=0 or 1; p=1 or 2; and q=0, 1 or 2; with the provisos that $1 \leqq w+x \leqq 2$, $1 \leqq q+z \leqq 2$, and $p \cdot y=p(m+2n)+(p-1)(x+z)+q+w+x+z-2$; and wherein R includes the halogens having an atomic number greater than 9, and radicals having a valence of 1, and wherein R' is a group having a valence of 2, and a process for preparing the compound.

8 Claims, No Drawings

CHEMICAL COMPOUNDS HAVING TWO TRIFLUOROMETHYL GROUPS

This application is a continuation of U.S. patent application Ser. No. 08/864,522 filed May 28, 1997 (now abandoned).

FIELD OF INVENTION

This invention relates to fluorinated compounds bearing two trifluoromethyl groups and a method for preparing them. More specifically, the invention relates to aliphatic compounds having two terminal trifluoromethyl groups and at least one reactive functional group and to a method for preparing such aliphatic compounds.

BACKGROUND OF THE INVENTION

Compounds bearing one or more trifluoromethyl groups are used in a number of applications and are particularly well suited for imparting beneficial properties in polymers, or enhanced effectiveness in agricultural products and pharmaceuticals. For example, compounds such as trifluoroethanol and its esters, trifluoroacetic acid and its esters, 1,1,1 trifluoroacetone, and hexafluoroacetone are used to improve surface tension, chemical resistance and thermal stability in the synthesis of various types of polymers. Because of the beneficial properties of such known compounds, identifying new trifluoromethylated compounds and methods for preparing them is desirable.

Various trifluoromethylated compounds tend to be nonreactive and chemically resistant. Although such properties in the compounds are desired for some applications, there are other applications in which reactive compounds are preferred. For this purpose, the compounds should be conveniently functionalized; that is, include at least one functional group which is relatively reactive with one or more other materials. Ideally, methods for synthesizing the aforementioned types of trifluoromethylated compounds should be efficient and economical.

Methodologies for conveniently functionalizing trifluoromethylated compounds are not well defined. Moreover, often in the functionalization process, the trifluoromethyl group is disrupted and the selectivity tends to be poor. Therefore, there is a need to identify and provide synthesis methods for novel trifluoromethylated compounds that are conveniently functionalized and that can be synthesized economically.

DESCRIPTION OF THE INVENTION AND PREFERRED EMBODIMENTS

The present invention provides for a family of conveniently-functionalized, aliphatic-acyclic compounds bearing two terminal trifluoromethyl groups. This family can be derived from a readily synthesized, relatively inexpensive trifluoromethylated starting material, which is functionalized with high selectivity using commercially-available materials. More specifically, the present invention, among other aspects, provides for the functionalization of the trifluoromethylated starting material, which is relatively inert, to form a compound having relatively reactive halogen functionality. This halogen functionality provides a convenient "handle" in the form of a reactive group which can be reacted with other materials to form a host of other useful trifluoromethylated chemical compounds.

Conveniently-functionalized, trifluoromethylated chemical compounds include compounds represented by the formula:

$$CF_3CH_{2-w}(H_{1-x}CH_{2-y}R_mR'_nCH_{1-z})_pH_{2-q}CF_3 \quad (1)$$

wherein w=0, 1 or 2; x=0 or 1; y=0, 1 or 2; m=0, 1 or 2; n=0 or 1; z=0 or 1; p=1 or 2; and q=0, 1 or 2; with the provisos that $1 \leqq w+x \leqq 2$, $1 \leqq q+z \leqq 2$, and $p \cdot y=p(m+2n)+(p-1)(x+z)+q+w+x+z-2$; and wherein R includes the halogens having an atomic number greater than 9 and radicals having a valence of 1, such as, for example, hydroxyl, methoxyl, and aminyl and wherein R' is a group having a valence of 2, such as, for example, oxygen, sulfur and methylene. The preferred embodiment of the invention is a five carbon molecule, that is, p=1, simplifying Formula 1 to Formula 2 below:

$$CF_3CH_{2-x}CH_{2-y}R_mR'_nCH_{2-z}CF_3 \quad (2)$$

wherein, as above, x=0 or 1; y=0, 1 or 2; z=0 or 1; m=0, 1, or 2; and n=1 or 2; but with the proviso that y=m+2n+x+z. More preferably, R is chlorine, hydroxyl and/or methoxyl, and R' is oxygen. Particularly preferred compounds of formula 2 include a group 1 wherein x=0, y=2, z=0, and either m=2, such as, for example, 3,3-dichloro-1,1,1,5,5,5-hexafluoropentane ($CF_3CH_2CCl_2CH_2CF_3$), or n=1, such as, for example, 1,1,1,5,5,5-hexafluoropentan-3-one ($CF_3CH_2COCH_2CF_3$); a group 2 wherein x=0, y−1, and z=0, such as, for example, 1,1,1,5,5,5-hexafluoropentan-3-ol ($CF_3CH_2CH(OH)CH_2RCF_3$); a group 3 wherein x=1, y=1, and z=0, such as, for example, cis and trans 3-chloro-1,1,1,5,5,5-hexafluoropent-3-ene (E/Z-$CF_3CH{=}CClCH_2CF_3$) and 3-methoxy-1,1,1,5,5,5-hexafluoropentant-2-ene ($CF_3CH{=}C(OCH_3)CH_2CF_3$), and a group 4 wherein x=1, y=2, and z=1, such as 1,3-bis(trifluoromethyl)allene ($CF_3CH{=}C{=}CHCF_3$).

The present invention also provides a process for synthesizing the compounds of Formula 1 utilizing an aliphatic hydrofluorocarbon (HFC) starting material bearing two terminal trifluoromethyl groups and at least one difluoromethylene group between the terminal trifluoromethyl groups. A suitable starting material has the following formula.

$$CF_3(CH_2CF_2)_qF \quad (3)$$

wherein q=2 or 3.

The preparation of the HFC of Formula 3 is known in the art and is taught, for example, in U.S. Pat. No. 5,395,997 issued to Van Der Puy et al., incorporated herein in its entirety by reference. According to this disclosure, the HFC is prepared in a two-step process. First, $CCl_4$ is added to vinylidene chloride to form a hydrochlorocarbon, for example, 1,1,1,3,3,5,5,5-octachloropentane. Next, the hydrochlorocarbon is fluorinated to form the HFC of Formula 3, for example, 1,1,1,3,3,5,5,5-octafluoropentane. The materials required for this process are readily available and relatively inexpensive.

Although the hydrofluorocarbon of Formula 3 bears two trifluoromethyl groups and is derived from convenient materials, its relative inertness tends to render it unsuitable as a starting material for synthesizing other compounds. That is, the compound's saturated bonds are relatively stable compared to, for example, allylic or benzylic systems, and its nonactivated $CF_2$ and $CF_3$ groups are relatively inert compared to other functional groups.

The present invention involves an innovative process of converting at least one difluoromethylene group the HFC of Formula 3 to form a conveniently functionalized compound while maintaining the two trifluoromethyl groups. More specifically, the process involves a halogen exchange with the fluorine atoms of the difluoromethylene group to form a compound of Formula 1, wherein x=O, y=O, z=O, m=2, and R is a halogen having an atomic number greater than 9.

In the preferred embodiment, the fluorine is exchanged with chlorine to form a hydrochlorofluorocarbon (HCFC) compound having two trifluoromethyl groups and at least one dichloromethylene group. The HCFC is represented by Formula 1, wherein x=0, y=2, z=0, m=2, and n=0 and wherein R is chlorine, or, in simpler terms, by the formula:

$$CF_3(CH_2CCl_2)_dCH_2CF_3 \quad (4)$$

wherein d=1 or 2.

Halogen exchange with the fluoromethlyene group of HFC of Formula 3 is performed by treating the compound with a halogen exchange agent. Suitable halogen exchange agents include, for example, $AlCl_3$, $BCl_3$ and AlBr. It is preferable to use a molar excess of the halogen exchange agent relative to the HFC of Formula 3.

The halogen exchange reaction is preferably cooled using known means such as an ice bath. In the preferred embodiment, the reaction temperature is maintained at about −5° to about 10° C., and more preferably at about 0° C. to about 5° C. At reaction temperatures of 0° to about 5° C., reaction times are typically about 5 h and increase as the temperature is decreased below 0° C.

In a more preferred embodiment, 1,1,1,3,3,5,5,5-octafluoropentane is treated with a molar excess of $AlCl_3$ in solution with $CH_2Cl_2$ to convert it, with good selectivity, to 3,3-chloro-1,1,1,5,5,5 hexafluoropentane (HCFC-456) ($CF_3CH_2CCl_2CH_2CF_3$). By maintaining the reaction temperature at about 0–5° C. and using a molar ratio of $AlCl_3$ to octafluoropentane of about 2, HCFC-456 may be obtained with about 72% distilled yield and with a purity of about 98% or better. Monochlorinated materials, for example, $CF_3CH_2CFClCH_2CF_3$, are produced only in trace quantities as identified by GC-MS. By-products include materials resulting from the exchange of fluorine for chlorine in the $CF_3$ groups and were primarily the unsaturated compounds E/Z-$CF_3CH_2CCl{=}CHCCl_3$ and E/Z-$CCl_3CH{=}CClCH{=}CCl_2$. At temperatures above 5° C., the selectivity for HCFC-456 decreases significantly.

Since the $CCl_2$ group which is present in HCFC-456 is substantially more reactive relative to the $CF_3$ groups, the HCFC of Formula 3, particularly HCFC-456 , can be used to prepare other useful compounds while maintaining the terminal trifluoromethyl groups. For example, the HCFC may be converted to form ketones, diketones, alcohols, amines, ethers, olefins, and diolefins using process mechanisms that exploit the $CCl_2$ group.

The discussion below describes the preparation of olefins, diolefins, ethers, ketones and alcohols. In this description, particular emphasis is placed upon the syntheses of $CF_3CH_2COCH_2CF_3$, $CF_3CH_2CH(OH)CH_2CF_3$, cis and trans $CF_3CH{=}CClCH_2CF_3$, $CF_3CH{=}C{=}CHCF_3$, and $CF_3CH{=}C(OCH_3)CH_2CF_3$ from HCFC-456. It should be noted, however, that other process mechanisms are possible to produce these and other compounds of Formula 1.

The HCFC of Formula 3 may be dehydrochlorinated to form olefins, diolefins (or dienes), and other unsaturated compounds of Formula 1. The dehydrochlorination may be performed in a variety of ways including, for example, thermal, catalytic and alkaline dehydrochlorination, and combinations thereof Catalytic thermal dehydrochlorination may be performed using known apparatus and techniques. A satisfactory apparatus consists of a single reaction vessel, such as an autoclave, to which the starting material can be supplied in liquid or gaseous form, and which can be heated or cooled well enough to maintain the reaction temperature at a desired temperature. In the vapor phase, the reaction occurs at elevated temperatures over a dehydrohalogenation catalyst. Suitable catalysts are known in the art and include, for example, activated carbon, $Cr_2O_3$, and $TiO_2$. The reactor is maintained at a temperature preferably between about 200 to about 350° C., and more preferably between about 250 to about 300° C.

In a preferred embodiment, HCFC-456 is dehydrofluorinated in the vapor phase to form cis and trans 3-chloro-1,1,1,5,5,5-hexafluoropent-3-ene (E/Z-$CF_3CH{=}CClCH_2CF_3$). When activated carbon is used as the catalyst and the reactor is maintained at between about 260° C. and about 270° C., a conversion of about 47% and a selectivity of about 96% or more can be realized. Although liquid phase dehydrochlorination is possible, it typically results in lower selectivities than the vapor phase process.

A diene of Formula 1 may also be produced as a secondary product in the dehydrochlorination of HCFC of Formula 3. Generally, the formation of the diene is greater in the liquid phase dehydrochlorination. Higher temperatures and longer residence times in the vapor phase dehydrochlorination, however, will increase the amount of the diene produced.

As an alternative to or in combination with thermal dehydrochlorination, the HCFC of Formula 3 or an olefin of Formula 1 may be contacted with a base to effect dehydrochlorination. Suitable bases are generally organic and include, for example, tertiary amines such as triethylamine. Preferably, the base is in a suitable reaction solvent such as a polar aprotic solvent. The proportion of organic base to the HCFC or olefin depends upon the intended degree of dehydrochlorination. For example, if HCFC of Formula 3 is being dehydrochlorinated twice to form a diene, then a molar ratio of base to HCFC of about 2 is preferred. However, if the HCFC is being dehydrochlorinated only once to form an olefin or if an olefin is being dehydrochlorinated only once to form a diene, then a molar ratio of base to HCFC of about 1 is preferred.

In a preferred embodiment, 1,3-bis(trifluoromethyl)allene ($CF_3CH{=}C{=}CHCF_3$) is formed by twice dehydrochlorinating HCFC-456 or once dehydrochlorinating E/Z-$CF_3CH{=}CClCH_2CF_3$ using triethylamine in a polar aprotic solvent.

The diene of the present invention can be used to prepare an ether of Formula 1, preferably (3-methoxy-1,1,1,5,5,5-hexafluoropent-2-ene, ($CF_3CH{=}C(OCH_3)CH_2CF_3$)). To this end, an alcohol is added across one of the diene's double bounds. This may be accomplished, for example, by reacting the diene with an alcohol having the formula ROH in the presence of a suitable catalyst such as, for example, RONa and ROK. Preferably, R is a low carbon alkyl group such as methyl or ethyl. The amount of catalyst used will generally range from about 5% to about 25 mol %. This reaction is generally performed under mild conditions, for example, at temperatures between about 10° to about 20° C.

A ketone of Formula 1 may be prepared in a number of ways. In one way, the HCFC of Formula 3 is hydrolyzed using a Lewis acid to form the ketone. Suitable Lewis acids include, for example, mercuric oxide, mercuric acetate, and mercuric trifluoroacetate, and a mixture of two or more of the aforementioned. Preferably, HCFC-456 is treated with a solution of mercury salt and acid to form a ketone having the formula $CF_3CH_2C(O)CH_2CF_3$. In a more preferred embodiment, the solution comprises mercuric oxide in concentrated sulfuric acid. Other mercury salts may be used such as mercuric acetate or trifluoroacetate and the sulfuric acid may be replaced with trifluoroacetic acid. However, the latter reagents are typically more expensive and their use tends to result in lower selectivities for the ketone. In the preferred embodiment, the molar ratio of mercury to HCFC-456 is about 1 to about 2 and, in the more preferred embodiment, is about 1.

The temperature at which the hydrolysis is conducted and the period of reaction will depend on the particular HCFC and Lewis acid used. One of ordinary skill in the art can readily optimize the conditions of the reaction without undue experimentation to obtain the desired results. In the preferred embodiment, brief heating, such as, for example, 0.5 to about 1.5 h at about 60 to about 70° C., is beneficial in reducing the reaction time. If 100% sulfuric acid is used, no heating is required since the reaction produces a modest exotherm as the reaction progresses. The yield of ketone is generally 55–65%.

Alternatively, the ketone of the present invention can be prepared by using an olefin of Formula 1 as a starting material. In one embodiment, the ketone $CF_3CH_2C(O)CH_2CF_3$ is prepared from E/Z-$CF_3CH{=}CClCH_2CF_3$ using the procedure employed for the conversion of HCFC-456 to the ketone as described above. While this process produces a ketone with high selectivity, the use of HgO is environmentally undesirable for large scale operations. Consequently, an alternative, environmentally acceptable procedure is preferred. To this end, the present invention encompasses an alternative process of preparing the ketone using a methyl vinyl ether. The methyl vinyl ether may be hydrolyzed to form a ketone. For example, in one preferred embodiment, $CF_3CH{=}C(OCH_3)CH_2CF_3$ is hydrolyzed to form the ketone $CF_3CH_2C(O)CH_2CF_3$. This has certain advantages over the hydrolysis method described above, such as, for example, eliminating the need for environmentally problematic or undesirable mercury compounds.

Reducing ketones within the scope of the present invention results in the formation of alcohols of Formula 1, preferably $CF_3CH_2CH(OH)CH_2CF_3$. The reduction can be performed using known methods and techniques which one skilled in the art would be able to determine without undue experimentation. In a preferred embodiment, 1,1,1,5,5,5-hexafluoropentan-3-one is reduced to form 1,1,1,5,5,5-hexafluoropentan-3-ol using any one of many well-known reducing procedures. Reducing the ketone using sodium borohydride in water is particularly convenient since the product is insoluble and could be isolated directly in good yield (for example, 91%) and purity.

The temperature at which the reduction reaction is performed and the period of reaction will depend on the starting material and reducing agent. Again, one of ordinary skill in the art can readily optimize the conditions of the reaction without undue experimentation to obtain the desired results. When using sodium borohydride in water, a reaction temperature of about 0° C. and a reaction time of about one hour or less are typical.

Given their convenient functionality and terminal trifluoromethyl groups, the compounds of the present invention lend themselves to a variety of applications. For example, the olefins and diolefins, aside from intermediates in the production of ketones, have other potential uses, for example, as monomers in polymerization reactions. Other compounds like the ketone $CF_3CH_2C(O)CH_2CF_3$ and its corresponding alcohol, $CF_3CH_2CH(OH)CH_2CF_3$, are versatile raw materials. Their value as intermediates is indicated by the usefulness of compounds having just one trifluoromethyl group. These perfluoroalkyl acetones ($RfC(O)CH_3$) have been the subject of recent investigations with respect to their utility as chemical intermediates (M. A. Kurykin, I. M. Volpin, L. S. German, J. *Fluorine Chem.,* 80 (1996) 9–12). For example, the Baeyer-Villiger oxidation of trifluoromethyl ketones (CF3C(O)R) provides a means to obtain esters of trifluoroacetic acid (T. Kitazume, J. Kataoka, J. *Fluorine Chem.,* 80 (1996) 157–8). By analogy with Kitazume and Kataoka's work, a Baeyer-Villiger oxidation of the ketone provides $CF_3CH_2OC(O)CH_2CF_3$, which is an ester of trifluoroethanol and trifluoropropionic acid. Still other uses of these intermediates will be apparent to those skilled in the art.

EXAMPLES

The following examples illustrate the practice of the present invention, specifically, the preparation of a family of conveniently-functionalized, aliphatic compounds bearing two terminal trifluoromethyl groups.

Example 1

This example illustrates the preparation of 3,3-dichloro-1,1,1,5,5,5-hexafluoropentane and 3-chloro-1,1,1,5,5,5-hexafluoropent-3-ene and 1,1,1,3,5,5-hexachloropent 1,3-diene.

To 125 mL $CH_2Cl_2$, cooled in an ice bath, were added 33.5 g (0.251 mol) $AlCl_3$, followed by the dropwise addition over 0.5 h of 25.7 g (0.119 mol) $CF_3CH_2CF_2CH_2CF_3$. Stirring was continued at ice-bath temperature for an additional 5 h before quenching the reaction by adding the mixture to 500 mL ice and water. The aqueous layer was extracted with 25 mL $CH_2Cl_2$, and the combined organic layers were washed with 50 mL water and dried using $Na_2SO_4$. Gas chromatography analysis indicated a conversion of 98% and a selectivity of 91%. Distillation gave 21.4 g (72% yield) of >99% pure $CF_3CH_2CCl_2CH_2CF_3$, boiling point 110° C. $^1H$ NMR: 3.3 (q, J=9 Hz) ppm. $^{19}F$ NMR: −61.5 (t, J=9 Hz) ppm. MS: 248 (P, 0.01), 215 (P—Cl, 28.8), 213 (P—Cl, 85.6), 167 ($CF_3CH_2CCl_2$, 12.2), 165 ($CF_3CH_2CCl_2$, 19.7), 151 (16.2), 149 (51.8), 133 (49.0).

The by-product E/Z-$CF_3CH_2CCl{=}CHCCl_3$ had the following properties: boiling point 80–90° C. at 50 mm Hg. For the major isomer, $^1H$ NMR: 6.74 (s), 3.45 (q, J=8.5–9.0 Hz) ppm. $^{19}F$ NMR: −61.6 (t, J=8.5–9.0 Hz) ppm. For the minor isomer, $^1H$ NMR: 6.94 (s), 3.18 (q, J=9.5–9.8 Hz). $^{19}F$ NMR: −65.1 (t, J=9.5–9.8 Hz) ppm. The mass spectra for the two isomers, having a weak molecular ion at m/z 260, were nearly identical.

The by-product E/Z-$CCl_3CH{=}CClCH{=}CCl_2$ had the following properties: boiling point 150–151° C. at 47 mm Hg; $^1H$ NMR: one isomer, 6.94 (s) and 6.41 (s) ppm, the other isomer, 6.80 (d, J=1.7 Hz) and 6.69 (d, J=1.7 Hz) ppm. The mass spectra for the two isomers were virtually identical: 272 (P, 1.31), 274 (P+2, 2.0), 276 (P+4, 1.6), 278 (P+6, 0.6), 237 (PCl, 65.7), 239 (P+2-Cl, 100), 241 (P+4- '1, 67.5), 243 (P+6-Cl, 17.6).

Example 2

This example describes a vapor phase process for the preparation of 3-chloro-1,1,1,5,5,5-hexafluoropent-3-ene.

HCFC-456 (13.5 g/h) diluted with nitrogen (25 cc/min) was passed over 50 cc Darco 12–20 mesh activated carbon at 266° C. A conversion of 47% was realized with a selectivity for $C_5H_3ClF_6$ isomers of 96%. At 315° C., the conversion increased to 98%, while the selectivity decreased to 84%. E/Z-$CF_3CH{=}ClCCH_2CF_3$ distilled at 81–92° C. A distillation cut having a boiling point of 83–85° C. contained the isomers in a 3:1 ratio, which changed to approximately 1:3 at 92–96° C. Spectra analysis taken on the different distillation cuts allowed the following assignments to be made: the lower boiling isomer: $^1$H NMR: 6.21 (1H, q, J=7 Hz) and 3.4 (2H, q, J=9 Hz) ppm. $^{19}$F NMR: −59.3 (d, J=7 Hz) and −64.5 (t, J=9 Hz) ppm (minor F—F coupling (ca. 2 Hz) also observed); the higher boiling isomer: $^1$H NMR: 6.06 (1H, q, J=7 Hz) and 3.2 (2H, q, J=9.6 Hz) ppm. $^{19}$F NMR: −61.3 (d, J=7 Hz), −65.6 (t, J=9.6 Hz) ppm. MS: 212 (P, 60.6), 214 (]+2, 19.3), 193 (P—F, 26.9), 195 (P+2-F, 8.6), 177 (P—Cl, 38.9), 113 (96.2), 69 (100).

Example 3

This example describes a liquid phase process for the preparation of 3-chloro-1,1,1,5,5,5-hexafluoropent-3-ene. The process also produced 1,3-bis(trifluoromethyl)allene.

A mixture of 100 mL dimethylformamide, 24 g triethylarnine, and 50.0 g HCFC-456 was heated to 65–70° C. for 3 hours and at 80–90° C. for an additional 2 hours. The cooled slurry was poured into 500 mL cold 0.4 N HCl. The organic layer was separated and washed with 50 mL water to give 37.5 g of crude product, which by GC analysis, indicated a conversion of 92.6% and a selectivity for E/Z-$CF_3CH{=}CClCH_2CF_3$ of 77%. The higher boiling isomer was obtained in 96% purity from a distillation fraction boiling at 92° C.

A secondary product, 1,3-bis(trifluoromethyl)allene ($CF_3CH{=}C{=}CHCF_3$) was also recovered. It had a boiling point of 44–45° C. FT-IR: 3056, 2004, 1304, 1278, 1255, 1138 cm$^{-1}$. MS: 176 (P, 100). $^{13}$C NMR: 206.8 (m, $J_{C-F}$=~6 HZ), 121.6 (q, $J_{C-f}$=275.2 HZ), 92.9 (q, $J_{C-F}$=39 HZ) ppm. $^1$H NMR: 5.97 (heptet, J=4.6 HZ) ppm. $^{19}$F NMR: −61.5 (t, J=4.6 HZ) ppm.

Example 4

This example shows the preparation of 1,3-bis (trifluoromethyl)allene from HCFC-456.

A mixture of 240 mL DMF and 48.2 g (0.48 mol) triethylamine was heated to 59° C. in an oil bath. To the bath, 59.9 g (0.24 mol) of HCFC-456 were added, and heating of the bath continued for 3.0 h. The reaction was quenched by adding the rapidly cooled reaction mixture to 1 L cold 0.4 N HCl. The two-phase mixture was cooled to 5–10° C. and the lower layer (42.0 g) was separated and dried. Distillation provided 19.5 g of 99% pure $CF_3CH{=}C{=}CHCF_3$, boiling point 45–46° C. and 6.6 g of cis and trans 3-chloro-1,1,1,5,5,5-hexafluoropent-3-ene for a yield of 52%, based on unrecovered cis and trans 3-chloro-1,1,1,5,5,5-hexafluoropent-3-ene. FT-IR: 3056, 2004, 1304, 1278, 1255, 1138 cm$^{-1}$. MS: 176 (P, 100). $^{13}$C NMR: 206.8 (m, $J_{C-F}$=~6 HZ), 121.6 (q, $J_{C-F}$=275.2 HZ), 92.9 (q, $J_{C-F}$=39 HZ) ppm. $^1$H NMR: 5.97 (heptet, J=4.6 HZ) ppm. $^{19}$F NMR: −61.5 (t, J=4.6 HZ) ppm. Anal. Calcd for $C_5H_2F_6$: C, 34.11; H 1.14. Found: C, 34.11; H 1.13.

Example 5

This example describes the preparation of 3-methoxy-1,1,1,5,5,5-hexafluoropent-2-ene from bis(trifluoromethyl) allene 21.1 g (0.12 mol) of bis(trifluoromethyl)allene were added to 20 mL 0.5 N $NaOCH_3$ in methanol (8 mol % relative to allene) over 1 h with water bath cooling, keeping the reaction temperature at 10–20° C. Stirring was continued for 15 min. and the mixture poured into 80 mL cold water. The lower layer was separated and the aqueous portion extracted with 20 mL $CH_2Cl_2$. The combined organic layers were washed with 5 mL brine, dried ($Na_2SO_4$) and distilled to give 21.9 g (88% yield) of $CF_3CH{=}C(OCH_3)CH_2CF_3$, boiling point 110–111° C. IR: 1672 cm$^{-1}$. Major MS fragments: 208 (75.9), 189 (30.2), 158 (31.6), 125 (60.5), 111 (82.4), 91 (100), 31 (91.2). 1H NMR:4.95 (q,1H, J=7.5 Hz), 3.65 (s, 3H), 3.18 (q, 2H, J=9.8 Hz) ppm. $^{19}$FNMR: −54.4 (d,3 F), −63.9 (t, 3 F) ppm. Anal. Calcd for $C_6H_6F_6O$: C, 34.61; H, 2.91. Found: C, 34.59; H. 2.85.

Example 6

This example describes the preparation of 1,1,1,5,5,5-hexafluoropentan-3-one using 3-methoxy-1,1,1,5,5,5-hexafluoropent-2-ene.

The vinyl methyl ether, 3-methoxy-1,1,1,5,5,5-hexafluoropent-2-ene, (21.3 g, 102 mmol) was added to 20 mL (36 g) concentrated $H_2SO_4$ at 15–20° C. over 15 min Stirring was continued for 10 min. and the reaction mixture poured into 100 mL cold water. The product was extracted with 2×40 mL ether. The combined extracts were washed with brine, dried ($Na_2SO_4$) and distilled to give 15.3 g (77% yield) of 1,1,1,5,5,5-hexafluoropentan-3-one, bp 122–123° C.

Example 7

This example shows the preparation of 1,1,1,5,5,5-hexafluoropentan-3-one from 3,3-dichloro-1,1,1,5,5,5-hexafluoropentane.

A mixture of 20 mL 100% $H_2SO_4$, 10.6 g (0.049 mol) HgO; and 12.0 g (0.048 mol) $CF_3CH_2CCl_2CH_2CF_3$ was shaken periodically over 45 min, during which time a thick, nearly white paste resulted. An exothermic reaction also occurred after approximately 10 min and subsided after about 0.5 h. The cooled reaction mixture was added to 75 g ice and 25 mL concentrated HCl. The lower liquid phase was separated and the aqueous layer was extracted with 3×35 mL ether. The combined organic extracts (including the original organic layer) were washed with 10 mL water, dried with $Na_2SO_4$ and distilled. Five and three tenths g (56% yield) of 97% pure $CF_3CH_2C(O)CH_2CF_3$ were obtained (boiling point 122–123° C.). $^1$H NMR: 3.4 (q, J=10.2 Hz). $^{19}$F NMR: −63.0 (t, J=10.2 Hz) ppm. IR: 1746 (C═O) cm$^{c-1}$. MS: 194 (3.4), 111 (100), 91 (17.5), 83 (21.8), 69 (11.9).

Example 8

This example describes the preparation of 1,1,1,5,5,5-hexafluoropentan-3-ol from 1,1,1,5,5,5-hexafluoropentan-3-one.

Sodium borohydride (0.8 g) was added to 15 ml water at 0 C. (ice bath). After the $NaBH_4$ had dissolved, 9.7 g of $CF_3CH_2C(O)CH_2CF_3$ were added. The ketone froze. The ice bath was removed until the mixture was warm enough to melt the ketone, and the ice bath cooling was resumed. The reaction was quenched after 1 h with the addition of 5 ml 2N HCl and 10 ml brine. The lower layer (8.9 g) consisted of 95% pure $CF_3CH_2CH(OH)CH_2CF_3$ (91% yield). Distillation increased the purity to 97%; boiling point 65 C. at 95 mm Hg. $^1$H NMR: 4.4 (pentet, 1H), 2.9 (s, 1H), 2.4 (m, 4H) ppm. $^{19}$F NMR: −64.2 (t, J=10 Hz) ppm. FT-IR: 3415 (OH), 1264, 1154 cm$^{-1}$. MS: 113 (64.8), 111 (18.6), 109 (10.8), 93 (91.4), 91 (14.2), 69(16.5), 65 (100), 64 (33.8), 49 (28.1), 29 (25.8). Anal. Calcd for $C_5H_6F_6O$: C, 30.63; H, 3.08. Found: C, 30,61; H, 3.11.

What is claimed is:

1. A compound having the formula:

$$CF_3CH_{2-x}(CH_{2-y}R_m)CH_{2-z}CF_3$$

wherein x=0 or 1; y=1 or 2; m=0, 1, or 2; and z=0 or 1 with the proviso that y=m+x+z; wherein R is selected from the group consisting of chlorine, hydroxyl, methoxyl and combinations of chlorine with itself or methoxyl, hydroxyl with itself or with methoxy and methoxyl with itself, with the proviso that when y=2 and m=1, R is not hydroxyl.

2. The compound of claim 1, wherein x=0, y=1, and z=0.

3. The compound of claim 2 having the formula $CF_3CH_2CH(OH)CH_2CF_3$.

4. The compound of claim 1, wherein x=1, y=2, and z=0.

5. The compound of claim 4 having the formula $CF_3CH{=}C(OCH_3)CH_2CF_3$.

6. The compound of claim 4 having the formula cis and trans $CF_3CH{=}CClCH_2CF_3$.

7. The compound of claim 1 having the formula $CF_3CH{=}C{=}CHCF_3$.

8. A compound having the formula:

$$CF_3CH_{2-x}(CH_{2-y}R_m)CH_{2-z}CF_3$$

wherein x=0 or 1; y=1 or 2; m=0, 1 or 2; and z=0 or 1 with the proviso that y=m+x+z; wherein R is selected from the group consisting of chlorine, methoxyl and combinations of two thereof.

* * * * *